United States Patent [19]
Vallée et al.

[11] Patent Number: 6,008,265
[45] Date of Patent: Dec. 28, 1999

[54] FLUORINATED IONIC SULFONYLIMIDES AND SULFONYLMETHYLIDES, PROCESS OF PREPARING SAME AND USE THEREOF AS PHOTOINITIATORS

[75] Inventors: Alain Vallée, Varennes; Michel Armand, Montréal, both of Canada; Xavier Ollivrin; Christophe Michot, both of Grenoble, France

[73] Assignees: Hydro-Québec, Montréal, Canada; Centre National de la Recherche Scientifique, Paris, France

[21] Appl. No.: 08/943,820

[22] Filed: Oct. 3, 1997

[30] Foreign Application Priority Data

Oct. 3, 1996 [CA] Canada ................... 2187046

[51] Int. Cl.$^6$ ................... C08F 2/50; C08F 4/42; C08F 4/00; G03C 1/52
[52] U.S. Cl. ................... 522/25; 522/29; 522/31; 522/32; 522/18; 522/15; 522/35; 522/59; 522/79; 522/153; 522/160; 522/167; 522/168; 522/169; 522/170; 522/173; 522/180; 522/181; 522/184; 522/188; 522/189; 430/270.1
[58] Field of Search ................... 522/25, 28, 29, 522/27, 31, 59, 32, 18, 15, 35, 79, 153, 160, 167, 168, 169, 170, 173, 180, 181, 184, 188, 189; 430/270.1; 528/21, 23, 52

[56] References Cited

U.S. PATENT DOCUMENTS

| | | |
|---|---|---|
| 3,632,843 | 1/1972 | Allen et al. . |
| 4,031,036 | 6/1977 | Koshar . |
| 4,049,861 | 9/1977 | Nozari ................... 428/220 |
| 4,115,295 | 9/1978 | Robins et al. ................... 528/90 |
| 4,920,182 | 4/1990 | Manser et al. ................... 525/438 |
| 4,957,946 | 9/1990 | Meir et al. ................... 522/59 |
| 5,364,738 | 11/1994 | Kondo et al. ................... 430/283 |
| 5,554,664 | 9/1996 | Lamanna et al. . |

*Primary Examiner*—Susan Berman
*Attorney, Agent, or Firm*—Oblon, Spivak, McClelland, Maier & Neustadt, P.C.

[57] ABSTRACT

An ionic compound comprising at least one group $A^+X^-$, comprising:

a cationic group $A^+$ selected from the group consisting of biaryliodonium, arylsulfonium, arylacylsulfonium, diazonium and organometallic cations comprising a transition metal complexed with at least one unsaturated cyclic compound comprising 4–12 carbon atoms, said cationic group being part of a polymer chain; wherein $X^-$ is an imide anion, $[FSO_2NSO_2R'_F]^-$ or $[R_FCH_2OSO_2NSO_2R'_F]^-$ or $[(R_F)_2CHOSO_2NSO_2R'_F]^-$, or a methylide anion $[FSO_2C(Q)SO_2R'_F]^-$, or a $[R_FCH_2OSO_2C(Q)SO_2R'_F]^-$ or $[(R_F)_2CHOSO_2C(Q)SO_2R'_F]^-$.

26 Claims, No Drawings

FLUORINATED IONIC SULFONYLIMIDES AND SULFONYLMETHYLIDES, PROCESS OF PREPARING SAME AND USE THEREOF AS PHOTOINITIATORS

BACKGROUND OF THE INVENTION a) Field of the Invention

The present invention concerns ionic compounds, their process of preparation and their use as photoinitiators for the cationic polymerization or cross-linking of monomers and prepolymers, or for the modification of solubility parameters of certain polymers which may be used as photoresists.

b) Description of Prior Art

A polymerization which involves a mechanism of the cationic type has many advantages. In particular, it is fast, even at low temperature, the rate of utilisation of the monomer is high and sensitivity towards atmospheric contaminants such as oxygen is low as compared to free radical or anionic polymerizations.

Monomers, prepolymers and polymers containing cycloaliphatic epoxy functions and their vinyl ethers are increasingly used such as in the paint, varnish, inks, glue and anti-adhesive support industries. Moreover, vinyl ethers generally appear free of toxicity contrary to acrylates or methacrylates. Monomers and prepolymers of the epoxy type or of the vinyl ether type may be polymerized by different methods, cationic polymerization being particularly interesting.

Cationic polymerization catalysts are generally considered as acids within the meaning of Bronsted HX (proton donors), or as acids within the meaning of Lewis (receptors of electronic doublets), these operating in the presence of a co-catalyst which is a source of protons. These acids must be sufficiently strong to ensure stability to the cationic species which is either carried by the monomer or by the growing macromolecular chain, which means that the corresponding anion $X^-$ should possess a nucleophilic power which is as low as possible. The Bronsted acids which are most often used as catalysts for cationic polymerization are $CF_3SO_3H$, $HClO_4$, $HBF_4$, $HPF_6$, $HAsF_6$ and $SbF_6$. These acids are classified as follows with respect to initiation and propagation speeds, as well as obtention of the highest molecular weights:

$CF_3SO_3H < HClO_4 \approx HBF_4 < HPF_6 \approx HAsF_6 \approx SbF_6$

More recently, compounds with acid character such as bis(perfluoroalkylsulfonyl)-imide (U.S. Pat. No. 4,031,036, Koshar et al) or bis(perfluoroalkylsulfonyl)methane (U.S. Pat. No. 3,632,843, Allen et al) have also been used.

It is known that the preparation in situ of polymerization catalysts has many advantages. The production in situ of an acid which is capable of catalyzing the cross-linking of a monomer enables indeed to prepare a fluid monomer or a prepolymer (thermoplastic or solution) and to give it its final properties, for example by a simple treatment with a radiation. This technique is very much used for inks, paints, adhesive films and anti-adhesive films. It should also be noted that the preparation of the acid in situ from a salt enables in many cases to prevent the storing and handling of acid compounds which are more corrosive than the corresponding salts.

The catalysts may be prepared in situ by heat treatment. For example, ammonium or metal salts of bis (perfluoroalkylsulfonyl)imide (U.S. Pat. No. 4,031,036, Koshar et al) or ammonium or amine salts of bis (perfluoroalkylsulfonyl)methane (U.S. Pat. No. 3,632,843, Allen et al) have been used to obtain in situ, by heating, the corresponding bis(perfluoroalkylsulfonyl)-imide or bis (perfluoroalkylsulfonyl)methane, which thereafter acts as catalyst. These catalysts, so called "latent", however, only present a limited interest due to the necessity of an extended heating at high temperature to obtain a release of the acid, this release being in addition progressive and not integral with the initiation. On the one hand, the result is a low reaction speed and on the other hand, polymers of mediocre quality with respect to molecular weight, polydispersity and coloring.

The acid catalysts may also be prepared in situ by actinic radiation (such as photons whose wavelength corresponds to ultraviolet, visible, $\gamma$ and X radiation) or by $\beta$-radiation (beam electrons) on a suitable salt. Such a salt which is chemically labile under actinic or $\beta$-radiation bringing about the release of the corresponding acid with a strong catalytic activity, is a photoinitiator. The advantages of such a process are numerous: the release of the catalyst by radiation is rapid and practically complete, which causes a simultaneous initiation of the growth of the chains, and therefore a more homogeneous distribution of the masses with a lesser polydispersity, and better mechanical properties. The polymerization may be carried out at a relatively low temperature which prevents decomposition or coloring of materials obtained, as well as the formation of bubbles when a solvent is used or when the reaction mixture contains a volatile additive which is intended to be maintained in the final material and which plays the role of plasticizing agent U.S. Pat. No. 5,554,664 describes salts which can be activated under the effect of energy in which the cation comprises at least one cation selected from organometallic cations comprising an aromatic compound based on an arene or a pentadienyl ligand and a transition metal and also from iodonium, sulfonium, phosphonium and carbonium cations comprising a transition metal and in which the number of anions is sufficient to neutralize the charge of the cation, the anion being a tris(alkylsulfonylmethylide), a bis (alkylsulfonylimide), a tris(arylsulfonylmethylide) or a bis (arylsulfonylimide) salt in which the alkyl or aryl group is possibly perfluorinated or highly fluorinated. Salts of a simple metal, diazonium salts and ammonium salts are excluded. These salts may be used as photoinitiators for the cationic polymerization of olefins.

It is also known to use acids produced by actinic radiation to degrade the resins contained in a film constituting a photoresist. This technique is particularly efficient for photoresists with chemical amplification, in which a very small quantity of protons catalyzes the decomposition of groups such as esters containing a group derived from a tertiary alcohol (such as, for example, a tertiobutyl group), which is part of a macromolecular chain. This technique thus enables to modify the solubility parameters of a resin exposed to actinic radiation and to carry out operations of selective masking and engraving such as used in microelectronics.

SUMMARY OF THE INVENTION

The inventors have now found new ionic compounds which, under the action of an actinic or $\beta$-radiation, enable to give acids which have been found to be good catalysts for cationic polymerization or for modification of polymers.

It is therefore an object of the present invention to provide a new family of ionic compounds, a process for their preparation as well as their use as photoinitiators for the cationic polymerization or cross-linking of monomers, or for the modification of polymers, for example, when they are used as photoresists.

An ionic compound of the present invention contains at least one group A⁺X⁻ and it is characterized in that:

A⁺ is a cationic group selected from the group consisting of biaryliodonium, arylsulfonium, arylacylsulfonium, diazonium groups and organometallic cations comprising a transition metal complex with at least one unsaturated cycle comprising 4 to 12 carbon atoms, said cationic group possibly being part of a polymer chain;

X⁻ is an anion of an imide salt [FSO$_2$NSO$_2$R'$_F$]⁻ or [R$_F$CH$_2$OSO$_2$NSO$_2$R'$_F$]⁻ or [(R$_F$)$_2$CHOSO$_2$NSO$_2$R'$_F$]⁻, or a methylide anion [FSO$_2$C(Q)SO$_2$R'$_F$]⁻ or [R$_F$CH$_2$OSO$_2$C(Q)SO$_2$R'$_F$]⁻ or [(R$_F$)$_2$CHOSO$_2$C(Q)SO$_2$R'$_F$]⁻ in which:

1) Q represents:
   H—, Cl—, F—, Br— or CN—;
   an alkyl radical having 1 to 30 carbon atoms;
   an aryl or alkylaryl or arylalkyl radical having 6 to 30 carbon atoms;
   a group R"$_F$—, a group R"$_F$SO$_2$—, a group R"$_F$CH$_2$O—SO$_2$— or a group (R"$_F$)$_2$CHO—SO$_2$—;

2) R$_F$ and R'$_F$, as well as R"$_F$ possibly when X⁻ is a methylide anion, are independently selected from the group consisting of fluorine, perhaloalkyl groups having 1 to 30 carbon atoms, (perhaloalkyl)alkoxy groups having 2 to 30 carbon atoms, perhalogenated cycloaliphatic groups having 3 to 30 carbon atoms possibly containing heteroatoms selected from O and N and/or possibly carrying at least one perhaloalkyl chain, and perhalogenated aryl groups having 6 to 30 carbon atoms; or 3) R$_F$ and R'$_F$ together form a bivalent radical selected from perfluorinated linear alkylene radicals having 2 to 8 carbon atoms; or 4) when X⁻ is a methylide anion, R'$_F$ and R"$_F$ on the one hand, or R$_F$ and R"$_F$ on the other hand together form a bivalent radical selected from linear perfluorinated alkylene radicals having 2 to 8 carbon atoms.

As particularly interesting examples of anions X⁻, anions of sulfonimide salts [FSO$_2$NSO$_2$R'$_F$]⁻, [CF$_3$CH$_2$OSO$_2$NSO$_2$R'$_F$]⁻ and [(CF$_3$)$_2$CHOSO$_2$NSO$_2$R'$_F$]⁻, in which the radical R'$_F$ is F, CF$_3$CH$_2$O—, (CF$_3$)$_2$CH—O— or a perfluoroalkyl group having 1 to 10 carbon atoms (preferably CF$_3$—, C$_2$F$_5$—, C$_4$F$_9$—, C$_6$F$_{13}$—, C$_8$F$_{17}$— and C$_{10}$F$_{21}$—) may be mentioned.

Sulfonylmethylide anions [FSO$_2$C(Q)SO$_2$R'$_F$]⁻, [CF$_3$CH$_2$OSO$_2$C(Q)SO$_2$R'$_F$]⁻, [(CF$_3$)$_2$CHOSO$_2$C(Q)SO$_2$R'$_F$]⁻, in which R'$_F$ is F, CF$_3$CH$_2$O—, (CF$_3$)$_2$CH—O— or a perhaloalkyl group having 1 to 10 carbon atoms (preferably CF$_3$—, C$_2$F$_5$—, C$_4$F$_9$—, C$_6$F$_{13}$—, C$_8$F$_{17}$— and C$_{10}$F$_{21}$—) in which Q is selected from the group consisting of hydrogen, FSO$_2$—, CF$_3$CH$_2$—O—SO$_2$—, (CF$_3$)$_2$CH—O—SO$_2$—, alkyl, aryl, alkylaryl or arylalkyl groups having at most 30 carbon atoms, perfluoroalkylsulfonyl groups having 2 to 8 carbon atoms (preferably CF$_3$SO$_2$—, C$_2$F$_5$SO$_2$—, C$_4$F$_9$SO$_2$—, C$_6$F$_{13}$SO$_2$— and C$_8$F$_{17}$SO$_2$—) and perfluoroalkyl groups having 1 to 12 atoms carbon atoms (preferably CF$_3$—, C$_2$F$_5$—, C$_4$F$_9$—, C$_6$F$_{13}$—, C$_8$F$_{17}$— and C$_{10}$F$_{21}$—); or in which Q and R'$_F$ together form a bivalent perfluorinated linear alkylene group having 1 to 8 carbon atoms may be mentioned.

Among the anions defined above, those which are part of the group consisting of (FSO$_2$)$_2$N⁻, (FSO$_2$)$_3$C⁻, (FSO$_2$)$_2$CH⁻, (CF$_3$CH$_2$OSO$_2$)$_2$N⁻, [(CF$_3$)$_2$CHOSO$_2$]$_2$N⁻, (CF$_3$CH$_2$OSO$_2$)$_2$CH⁻, [(CF$_3$)$_2$—CHOSO$_2$]$_2$CH⁻, [(CF$_3$)$_2$CHOSO$_2$]$_3$C⁻, [(CF$_3$)$_2$CHOSO$_2$]$_3$C⁻, [FSO$_2$NSO$_2$—CF$_3$]⁻, [FSO$_2$NSO$_2$C$_2$F$_5$]⁻, [(CF$_3$)$_2$CHOSO$_2$NSO$_2$CF$_3$]⁻, [(CF$_3$)$_2$CHOSO$_2$NSO$_2$CF$_3$]⁻, [(CF$_3$)$_2$CHOSO$_2$NSO$_2$C$_2$F$_5$]⁻ and [CF$_3$CH$_2$OSO$_2$NSO$_2$C$_2$F$_5$]⁻ are particularly interesting A compound to the invention may be in the form of a monomer. It is then defined as a compound A⁺X⁻ in which X is such as defined previously and the cation A⁺ is represented by Formula

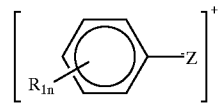

in which Z is selected from the group consisting of:
aryliodonium groups

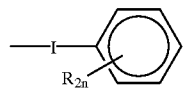

sulfonium groups

acylsulfonium group

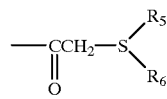

diazonium groups

organometallic groups

and in which R$_{1n}$ represents 1 to 4, preferably 1 to 2 groups which are identical or different and are bound to any free carbon atoms of the aryl group, R$_{2n}$ represents 1 to 4, preferably 1 to 2 groups which are identical or different and are bound to any free carbon atoms of the aryl groups, and groups R$_{1n}$, R$_{2n}$, and R$_3$ to R$_8$ are independently selected from:

- linear or branched alkyl or arylalkyl radicals having 1 to 30 carbon atoms;
- alkenyl radicals having 1 to 30 carbon atoms;
- aryl or alkylaryl radicals having 6 to 30 carbon atoms, including those which have condensed nuclei;
- radicals having 1 to 30 carbon atoms selected from the group consisting of oxaallkyls, azaalkyls, thiaalkyls, phosphaalkyls, oxaalkylenes, azaalkylenes, thiaalkylenes, phosphaalkylenes;
- radicals having 1 to 30 carbon atoms including a sulfoxide, sulfone, phosphine oxide, phosphonate group, all these radicals being obtained by addition of oxygen on the atoms of sulfur or phosphorus;

aromatic or alicyclic heterocyclic radicals comprising at least one heteroatom selected from the group consisting of O, N, S and P;

—NO, —CN, —OH, —Cl, —Br, —I, —F; or two substituents selected from $R_{1n}$ and/or two substituents selected from $R_{2n}$ or substituents $R_3$ and $R_4$, or substituents $R_5$ and $R_6$, which together form a bivalent radical which form a cycle with the group which carries it, said bivalent radical being selected from the group consisting of linear alkylene radicals having 1 to 18 carbon atoms, benzo biradicals possibly carrying at least substituent preferably selected from the group consisting of alkyl, oxaalkyl or alkenyl radicals having 1 to 10 carbon atoms, the oxaalkylene groups being represented by formula —R'—(OCH$_2$CH$_2$)$_q$—OR'— or —R'—[OCH(CH$_3$)CH$_2$]$_q$—OR'— in which R' is H or a linear alkylene radical having 1 to 18 carbon atoms and $1 \leq q \leq 22$.

The preferred monomer compounds are those in which the substituents $R_{1n}$, $R_{2n}$ and $R_3$ to $R_8$ are independently selected from the group consisting of linear alkyl radicals having 1 to 18 carbon atoms, 2-ethylhexyl, phenyl, oxaalkyls represented by formula R—(OCH$_2$CH$_2$)$_y$— or R—[OCH(CH$_3$)CH$_2$]$_y$— in which R is H or a linear alkyl radical having 1 to 18 carbon atoms and $1 \leq y \leq 22$.

The compounds of the present invention may also be in the form of polyionic oligomers or polymers made of a polycationic part $(A^+)_p$ comprising a plurality of ionium units and a number of anions $X^-$ sufficient to ensure electrical neutrality of the compound, the onium units being selected from the group consisting of biaryliodonium, arylsulfonium, arylacylsulfonium, diazonium, organometallic cations comprising a transition metal complexed with at least one unsaturated cycle comprising 4 to 12 carbon atoms.

A specific family of polyionic compounds according to the invention comprises polyiodonium salts in which a cationic part which comprises A$^+$units is associated with a number of anions X$^-$such as defined above, sufficient to neutralize the charge of the cationic part, said salts being represented by one of the following Formulae (I), (II), (III) or (IV):

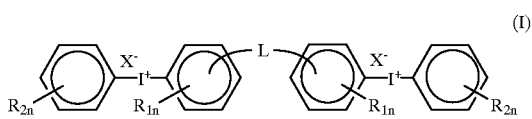
(I)

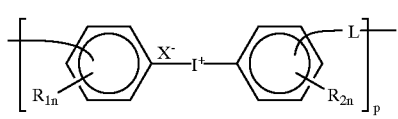
(II)

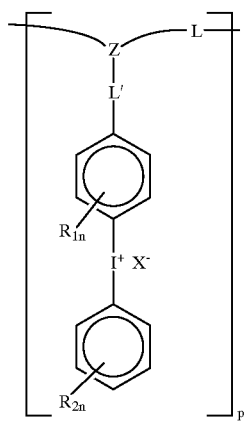
(III)

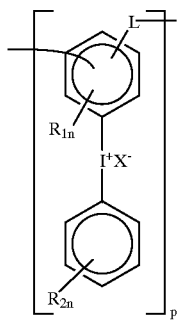
(IV)

in which:

a1) $R_{1n}$ and $R_{2n}$ have the meaning given above;

a2) L' represents a bivalent radical selected from the group consisting of linear alkylene radicals having 1 to 18 carbon atoms, substituted or non-substituted phenylene groups, oxaalkylene groups corresponding to formula —R'—(OCH$_2$CH2)$_q$—O—R'— or —R—[OCH(CH)CH$_2$]$_q$—O—R'— in which R' is a linear alkylene radical having 0 to 18 carbon atoms and $1 \leq q \leq 22$, —O—, —S—, >C=O siloxane groups —R'—O—[Si(R)$_2$O]$_r$—R'— or —O—[Si(R$_2$O]$_r$— in which $1 \leq r \leq 40$. R' has the meaning given above and R is a linear radical having 1 to 18 carbon atoms or 2-ethylhexyl or phenyl (preferably R=CH$_3$ or phenyl) or a direct bond between two carbon atoms of two non-condensed aryl groups;

a3) L represents a bivalent radical selected from the group defined in point a2) above for L'; or L represents a segment constituted by at least one non-ionic monomer unit or having an ionic group which is not sensitive to the action of actinic radiation (L in this case representing the average space between the active ionic groups);

a4) p represents the number of recurring units $2 \leq p \leq 1000$;

a5) Z represents CH, CR, N, SiR, SiRO$_3$, R being selected from linear alkyl radicals having 1 to 18 carbon atoms, 2-ethylhexyl and phenyl;

a6) X is such as defined previously.

Among the polyiodonium type compounds those in which the substituents $R_{1n}$ and $R_{2n}$ are independently selected from the group consisting of linear alkyl radicals having 1 to 18 carbon atoms, 2-ethylhexyl, phenyl, oxaalkyls corresponding to formula $R—(OCH_2CH_2)_y—$ or $R—[OCH(CH_3)CH_2]_y—$ in which R is a linear alkyl radical having 1 to 18 carbon atoms and $1 \leq y \leq 22$ are particularly preferred.

When the polyiodonium compound of the invention corresponds to Formulae (I) or (II), it is in the form of a dimer or a polymer comprising iodonium ionic group in the polymer chain.

When the polyiodonium compound corresponds to one of Formulae (III) or (IV), it is in the form of a polymer in which the iodonium ionic groups are carried by hanging substituents.

Another family of polyionic compounds according to the invention comprises polysulfonium salts in which a cationic part which comprises at least two units $A^+$ is associated with a number of anions $X^-$ such as defined above, sufficient to neutralize the charge of the cationic part, said salts being represented by one of the following Formulae (V), (VI), (VII), (VIII) or (IX):

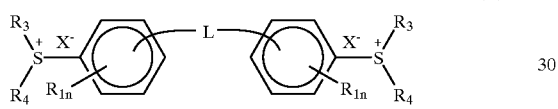
(V)

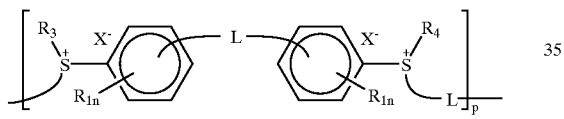
(VII)

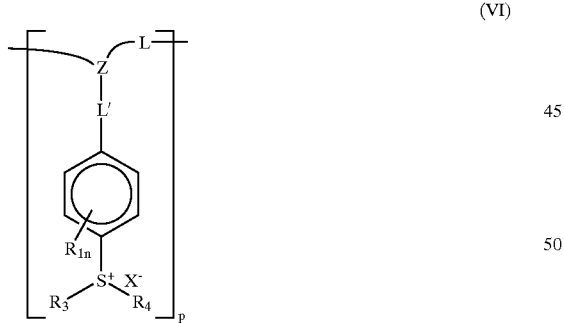
(VI)

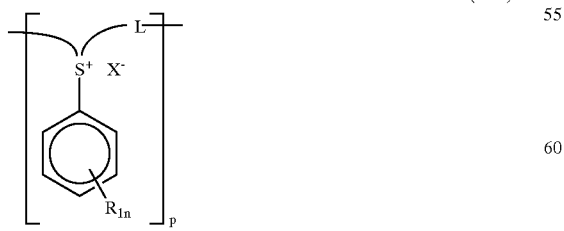
(VIII)

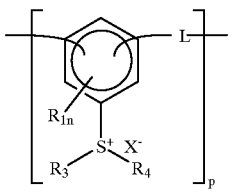
(IX)

in which:
b1) $R_{1n}$ represents 1 to 4, preferably 1 to 2 groups which are identical or different and are bound to any free carbon atoms of the aryl group, substituents $R_{1n}$ and substituents $R_3$ and $R_4$ being independently selected from:
linear or branched alkyl or arylalkyl radicals having 1 to 30 carbon atoms;
alkenyl radicals having 1 to 30 carbon atoms;
aryl or alkylaryl radicals having 6 to 30 carbon atoms including those which have condensed nuclei;
radicals having 1 to 30 carbon atoms selected from the group consisting of oxaalkyls, azaalkyls, thiaalkyls, phosphaalkyls, oxaalkylenes, azaalkylenes, thiaalkylenes, phosphaalkylenes;
radicals having 1 to 30 carbon atoms including a sulfoxide, sulfone, phosphine oxide, or phosphonate group, all these radicals being obtained by addition of oxygen on the atoms of sulfur or phosphorus;
aromatic or alicyclic heterocyclic radicals comprising at least one heteroatom selected from the group consisting of O, N, S and P;
—NO, —CN, —OH, —Cl, —Br, —I, —F;
or groups $R_3$ and $R_4$ carried by a same atom on the one hand and/or two substituents selected from $R_{1n}$ on the other hand together form a bivalent radical which forms a cycle with the group which carries it, said bivalent radical being selected from the group consisting of linear alkylene radicals having 1 to 18 carbon atoms, benzo biradicals possibly carrying at least one substituent preferably selected from the group consisting of alkyl, oxaalkyl or alkenyl radicals having 1 to 10 carbon atoms, and oxaalkylene groups corresponding to formula $—R'—(OCH_2CH_2)_q—O—R'—$ or $—R'—[OCH(CH_3)CH_2]_q—O—R'—$ in which R' is a linear alkylene radical having 0 to 18 carbon atoms and $1 \leq q \leq 22$;

b2) L' is such as defined in paragraph a2) above;
b3) L is such as defined in paragraph a3) above;
b4) p represents the number of recurring units, $1 \leq p \leq 1000$;
b5) Z represents CH, CR, N, SiR, $SiRO_3$, R being a linear alkyl radical having 1 to 18 carbon atoms or 2-ethylhexyl or phenyl;
b6) X is such as defined previously.

Polysulfonium compounds in which the substituents $R_{1n}$, $R_3$ and $R_4$ are selected from the group consisting of linear alkyl radicals having 1 to 18 carbon atoms, 2-ethylhexyl, phenyl, oxaalkyl corresponding to formula $R—(OCH_2CH_2)_y—$ or $R—[OCH(CH_3CH_2]_y—$ in which R is a linear alkyl radical having 1 to 18 carbon atoms and $1 \leq y \leq 22$, are particularly preferred.

When a polysulfonium compound of the invention corresponds to one of the Formulae (V), (VII) or (VIII), it is in the form of a polymer having ionic groups in the chain.

When a polysulfonium compound corresponds to one of Formulae (VI) or (IX), it is in the form of a polymer in which the ionic groups are carried by lateral groups.

Another family of polyionic compounds according to the invention comprises polysulfonium salts in which a cationic part which comprises at least two $A^+$ units is associated to a number of anions $X^-$ such as defined above sufficient to neutralize the charge of the cationic part, said salts corresponding to one of the following Formulae (X), (XI), (XII), (XIII), or (XIV):

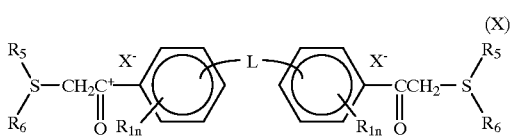
(X)

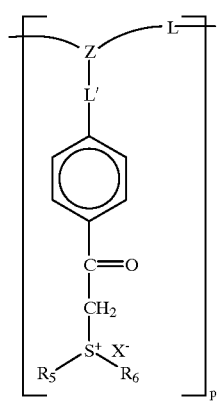
(XI)

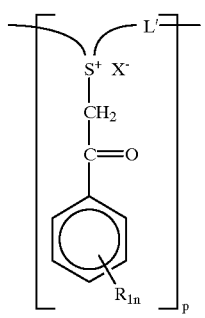
(XIII)

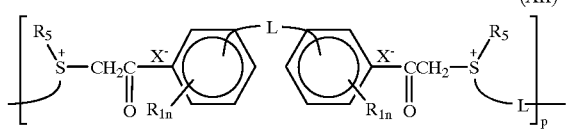
(XII)

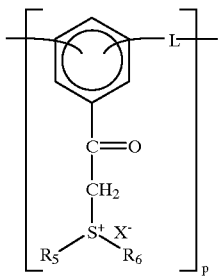
(XIV)

in which:
- c1) $R_{1n}$ has the meaning given above in paragraph b1) and the substituents $R_5$ and $R_6$ have the same meaning as the substituents $R_3$ and $R_4$ defined above in paragraph b1);
- c2) L' has the meaning given in paragraph a2) above;
- c3) L has the meaning given in paragraph a3) above;
- c4) p represents the number of recurring units, $1 \leq p \leq 1000$;
- c5) Z has the meaning given in paragraph a5) above;
- c6) X is such as defined previously.

Among the polyacylsulfonium compounds, those in which the substituents $R_{1n}$, $R_5$ and $R_6$ are selected from the group consisting of linear alkyl radicals having 1 to 18 carbon atoms, 2-ethylhexyl, phenyl, oxaalkyls corresponding to formula $R$—$(OCH_2CH_2)_y$ or $R$—$[OCH(CH_3)CH_2]_y$— in which R is a linear alkyl radical having 1 to 18 carbon atoms and $1 \leq y \leq 22$ are particularly preferred.

A fourth family of compounds according to the invention comprises salts in which the cationic part $A^{p+}$ is a polydiazonium corresponding to Formula (XV):

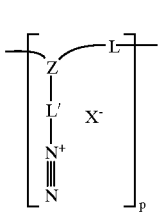
(XV)

in which:
- d1) L' has the meaning given in paragraph a2) above;
- d2) L has the meaning given in paragraph a3) above;
- d3) p represents the number of recurring units, $1 \leq p \leq 1000$;
- d4) X has the meaning given previously.

A fifth family of compounds according to the invention comprises organometallic polyonium compounds corresponding to one of the following Formulae:

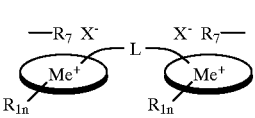
(XVI)

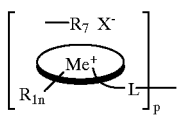

(XVII)

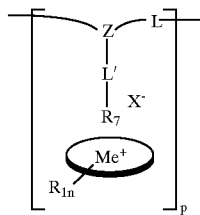

(XVIII)

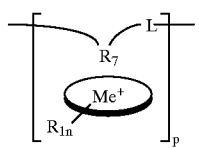

(XIX)

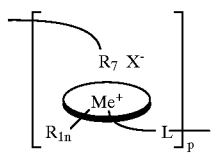

(XX)

in which:

e1) $R_{1n}$ has the meaning given in paragraph b1) above and substituent $R_7$ is selected from:
linear or branched alkyl or arylakyl radicals having 1 to 30 carbon atoms;
alkenyl radicals having 1 to 30 carbon atoms;
aryl or alkylaryl radicals having 6 to 30 carbon atoms including those which have condensed nuclei;
radicals having 1 to 30 carbon atoms selected from the group consisting of oxaalkyls, azaalkyls, thiaalkyls, phosphaalkyls, oxaalkylenes, azaalkylenes, thiaalkylenes, phosphaalkylenes;
radicals having 1 to 30 carbon atoms including sulfoxide, sulfone, phosphine oxide, phosphonate groups, all these radicals being obtained by addition of oxygen on the atoms of sulfur or phosphorus;
aromatic or alicyclic heterocyclic radicals comprising at least one heteroatom selected from the group consisting of O, N, S and P;
—NO, —CN, —OH, —Cl, —Br, —I, —F;

e2) L' has the meaning given in paragraph a2) above;

e3) L has the meaning given in paragraph a3) above;

e4) p represents the number of recurring units, $2 \leq p \leq 1000$;

e5) Z has the meaning given in paragraph a5) above;

e6) X has the meaning given previously;

e7) Me represents a transition metal selected from the group consisting of transition elements of columns 3 to 12 (lines 3 to 6) of the Periodic Classification.

As examples of compounds in which the cationic part is an organometallic polycation, polymers containing ferrocenium units (in particular those which include vinylferrocene, polyalkylbenzene-iron-cyclopentadiene units), polymers which include nickelocenium units, and polymers which include tricarbonyl manganesecyclopentadiene units may be mentioned.

Among compounds of the polymer type, particularly those for which $2 \leq p \leq 30$ are preferred.

The ionic compounds $A^+X^-$ or $(A^+X^-)_p$ of the present invention are in general insoluble in water. They may therefore be prepared by a process consisting in carrying out a metathesis in water or in water/light alcohol (methanol, ethanol, propanol) mixture between a soluble salt $A^+X_1^-$ or $(A^+X_1^-)_p$ in which $X_1^-$ is an anion of hydrophilic character, and a compound $A_1^+X^-$ soluble in water, $A_1^+$ being a cation which is highly hydrophilic.

The soluble salts $A^+X_1^-$ in which $A^+$ represents an iodonium, sulfonium, acylsulfonium, diazonium cation or an organometallic cation as defined above, and the soluble salts $(A^+X_1^-)_p$ in which $(A^+)_p$ represents a polyiodonium, polysulfonium, polyacylsulfonium or polydiazonium polycation, or an organometallic polycation, such as defined previously, are preferably selected from the salts in which the anion $X_1^-$ is a hydroxide, a chloride, a bromide, a hydrogenosulfate, a dihydrogenophosphate or a methylsulfonate. These anions being highly soluble in water or light alcohol, they promote solubility.

The compounds $A_1^+X^-$ which are soluble in water or in alcohol/water mixtures are preferably selected from sulfonimides and sulfonylmethanes of sodium, potassium, ammonium, calcium or magnesium. The choice of the cation depends of course on the ease of obtention and minimum hydrophilic character required to produce the solubility.

When a compound $A^+X^-$ or $(A^+X^-)_p$ of the invention is prepared from a salt $A^+X_1^-$ or $(A^+X_1^-)_p$ in which $X_1$ is a chloride, a bromide, an alkylsulfonate, an alkoxysulfonate or an arylsulfonate, in which the salts of sodium $NaX_1$ or potassium $KX_1$ are insoluble in the usual solvents, it is advantageous to carry out the reaction in the presence of an NaX or KX salt. The solubility of these salts in solvents even of average polarity being appreciable, the insoluble salts such as NaCl, KBr precipitate while the ionic compound of the invention remains in solution. As solvents, acetone, methylethylketone, acetonitrile, THF, esters such as formates or methyl or ethyl acetate may be mentioned.

It should be noted that any other process of ionic exchange may be used, for example a process which would use an ion exchange resin or a process of selective precipitation.

The inventors have surprisingly found that the compounds having fluorosulfonyl $FSO_2$ groups were stable in the presence of cations which are sensitive to actinic radiation in that the acids released were active to initiate reactions of polymerization or cross-linking by means of cation species. Moreover, the anions in which the negative charge is delocalized on the $FSO_2$ groups have been found to be capable of inducing remarkable solubilities of the corresponding salts in the usual solvents, comparable to those obtained with perifluoroalkyl groups. The anions containing one or more $FSO_2$ in replacement of perfluoroalkyl groups have, however, a lesser molecular weight and are therefore active at lower weight fractions. Their cost is more advantageous since the process does not require methods of chemical fluorination which have low yields. The same properties of solubility and activity during polymerization have been noted with compounds containing the groups $R_F$—$CH_2O$—$SO_2$— and $(R_F)_2CHO$—$SO_2$—, $R_F$ representing a fluoroalkyl group. Surprisingly, the carbon-oxygen bond of a group $R_F$—$CH_2O$—$SO_2$— or $(R_F)_2CHO$—$SO_2$— is stable during hydrolysis, contrary to what is observed with hydrocarbonated sulfonic esters (R—$CH_2O$—$SO_2$). In addition, anions comprising the groups $R_F$—$CH_2O$—$SO_2$— and $(R_F)_2CHO$—$SO_2$— are easily obtained from —$SO_2F$ or —SO$_2$Cl derivatives by the action of corresponding halogenated alcohols R$_F$CH$_2$OH and (R$_F$)$_2$CH$_2$OH which are produced industrially. Compared to analogous compounds having groups CF$_3$SO$_2$—, the compounds containing a group FSO$_2$ are less corrosive towards metals such as aluminum because they form a protective layer of fluoride which is an important element in the technology of paints. It appears that the groups R$_F$CHO$_2$—OSO$_2$— and (R$_F$)$_2$CHO—SO$_2$— have a behavior which is analogous to that of group FSO$_2$—.

It is also an object of the present invention to provide for the use of the ionic compounds of the invention as photoinitiators which are sources of Bronsted acids used as polymerization of cross-linking catalysts for monomers or polymers capable of cationic reaction or catalysts for the modification of polymers. The process of polymerization or cross-linking of monomers or prepolymers capable of cationic reaction is characterized in that there is used a compound of the invention as photoinitiator which constitutes a source of acid which catalyzes the polymerization reaction.

When compound A$^+$X$^-$ or (A$^+$X$^-$)$_p$ of the invention is intended to be used as photoinitiator for the polymerization of monomers or prepolymers which are polymerized by a cationic reaction, the choice of groups R$_1$ to R$_8$ is made among the above radicals in order to increase the solubility of said compound in the solvents which are used with the monomers or prepolymers and as a function of the desired properties of the final polymer. For example, the choice of non-substituted alkyl radicals gives a solubility in low polar medium. The choice of radicals comprising an oxa- or sulfone group gives a solubility in polar mixtures. The radicals including a sulfoxide, sulfone, phosphine oxide, phosphonate group obtained by addition of oxygen on the atoms of sulfur or phosphorus may confer to the polymer obtained, improved properties with respect to adhesion, brightness, resistance against oxidation or UV.

Among monomers of the cyclic ether or thioether type, ethylene oxide, propylene oxide, oxetane, epichlorhydrin, tetrahydrofuran, styrene oxide, cyclohexene oxide, vinylcyclohexene oxide, glycidol, butylene oxide, octylene oxide, glycidyl ether and esters (for example glycidyl methacrylate or acrylate, phenyl glycidyl ether, diglycidylether of bisphenol A or its fluorinated derivatives), cyclic acetals having 4 to 15 carbons (for example dioxolane, 1,3-dioxane, 1,3-dioxepane).

The monomers and prepolymers which may be polymerized or cross-linked with the photoinitiators of the present invention are those which may be subject to cationic polymerization.

Among monomers, monomers which include a cyclic ether function, a cyclic thioether function or a cyclic amine function, vinyl compounds (more particularly vinyl ethers), oxazolines, lactones and lactams, may be mentioned.

Among vinyl compounds, vinyl ethers constitute a very important family of monomers sensitive to cationic polymerization. By way of example, ethyl vinyl ether, propyl vinyl ether, isobutyl vinyl ether, octadecyl vinyl ether, ethyleneglycol monovinyl ether, diethyleneglycol divinyl ether, butanediol monovinyl ether, butanediol divinyl ether, hexanediol divinyl ether, ethyleneglycol butyl vinyl ether, triethyleneglycol methyl vinyl ether, cyclohexanedimethano monovinyl ether, cyclohexane-dimethanol divinyl ether, 2-ethylhexyl vinyl ether, poly-THF-divinyl ether having a molecular weight of between 150 and 5000, diethyleneglycol monovinyl ether, trimethylolpropane trivinyl ether, aminopropyl vinyl ether, 2-diethylaminoethyl vinyl ether may be mentioned.

Vinyl-methyl ethers which contain one or more CH$_3$CH=CH—O— groups and which are advantageously obtained by isomerization of the corresponding allyl ethers in the presence of a catalyst such as ($\phi_3$P)$_2$RuCl$_2$ may also be mentioned.

Other vinyl compounds may also be subject to a cationic polymerization in the presence of a polyionic compound according to the invention used as photoinitiators. By way of example, 1,1-dialkylethylenes (for example isobutene), aromatic vinyl monomers (for example styrene, α-alkylstyrene such as α-methylstyrene, 4-vinylanisole, acenaphthene), N-vinyl compounds (for example N-vinylpyrrolidone or N-vinylsulfonamides) may be mentioned by way of example.

Among the prepolymers, compounds in which epoxy groups are carried by an aliphatic chain, an aromatic chain or a heterocyclic chain, for example glycidyl ethers of bisphenol A which are ethoxylated by 3 to 15 ethylene oxide units, siloxanes having lateral groups of the type epoxycyclohexene-ethyl obtained by hydrosilylation of copolymers of dialkyl, alkylaryl or diaryl siloxane with methyl hydrogenosiloxane in the presence of vinylcyclohexane oxide, condensation products of the sol-gel type obtained from triethoxy or trimethoxy silapropylcyclohexene oxide, urethanes incorporating reaction products of butanediol monovinylether and of an alcohol having a functionality higher than or equal to 2 with an aliphatic or aromatic di-or triisocyanate, may be mentioned 34.

The process of polymerization according to the invention comprises a first step in which at least one monomer or prepolymer capable of cationic polymerization is mixed with at least one ionic compound A$^+$X$^-$ or (A$^+$X$^-$)$_p$ according to the invention, and a second step in which the mixture obtained is subject to actinic or β-radiation. Preferably, the reaction mixture is subject to radiation after having been formed into a thin layer having a thickness lower than 5 mm, preferably in the form of a thin layer having a thickness lower than or equal to 500 μm. The length of the reaction depends on the thickness of the sample and the power of the source at the active wavelength λ. It is defined by the speed at which it passes in front of the source, which is comprised between 300 m/min and 1 cm/min. Layers of the final material having a thickness higher than 5 mm may be obtained by repeating many times the operation consisting of spreading a layer and treating it with the radiation.

Generally, the quantity of photoinitiator used is between 0.01 and 15% by weight with respect to the weight of the monomer or prepolymer, preferably between 0.1 and 5% by weight.

An ionic compound A$^+$X$^-$ or (A$^+$X$^-$)$_p$ of the present invention may be used as photoinitiator in the absence of solvent, for example when it is intended to polymerize liquid monomers in which the salt is soluble or easily dispersible. This type of use is particularly interesting since it enables to overcome the problems associated with solvents (toxicity, flammability).

An ionic compound A$^+$X$^-$ or (A$^+$X$^-$)$_p$ of the present invention may also be used as photoinitiator in the form of a homogeneous solution in a solution which is inert towards polymerization, is ready to be used and is easily dispersible, in particular in the case where the mixture to be polymerized or cross-linked has an elevated viscosity.

As an example of inert solvent, volatile solvents such as acetone, methyl-ethyl ketone and acetonitrile may be mentioned. These solvents will be used merely to dilute the products to be polymerized or cross-linked (to make them less viscous, especially when dealing with a prepolymer).

They will be removed by drying after polymerization or cross-linking. Non-volatile solvents may also be mentioned. A non-volatile solvent will also be used to dilute the products which are intended to be polymerized or cross-linked, and to dissolve the salt $A^+X^-$ of the invention when used as photoinitiator, however it will remain in the material formed and will thus act as plasticizer. By way of example, propylene carbonate, γ-butyrolactone, ether-esters of mono-, di-, triethylene or propylene glycols, ether-alcohols of mono-, di-, triethylene or propylene glycols, plasticizers such as esters of phthalic acid or citric acid, may be mentioned.

According to another embodiment of the invention a compound which is reactive towards polymerization can be used as solvent or diluent, said compound having a low molecular weight and low viscosity, and can simultaneously act as polymerizable monomer and solvent or diluent for more viscous monomers or prepolymers jointly used. After the reaction, these monomers having been used as solvent are part of the finally obtained macromolecular network, their integration being more important when dealing with bifunctional monomers. The material obtained after radiation is free of products having a low molecular weight and a appreciable vapor pressure, or capable of contaminating the articles with which the polymers is in contact. By way of example, a reactive solvent may be selected from vinyl mono- and diethers of mono-, di-, tri- tetraethylene and propylene glycols, N-methylpyrrolidone, 2-propenylether of propylene carbonate sold for example under the trade name PEPC by ISP, New Jersey, U.S.A.

To radiate the reaction mixture, the radiation may be selected from ultraviolet radiation, visible radiation, X-rays, γ-rays and β-radiation. When ultraviolet light is used as actinic radiation, it may be advantageous to add to the photoinitiators of the invention photosensitizers intended to give an efficient photolysis with less energetic wavelengths than those corresponding to the maximum of absorption of the photoinitiator, such as those produced by industrial devices ($\lambda \approx 300$ nm for mercury vapor lamps in particular). Such additives are known, and by way of non-limiting examples, anthracene, diphenyl-9,10-anthracene, perylene, phenothiazine, tetracene, xanthone, thioxanthone, acetophenone, benzophenone, 1,3,5-triaryl-2-pyrazolines and their derivatives, and particularly derivatives which are substituted on the aromatic nuclei by means of alkyl, oxa- or azaalkyl radicals enabling among others to change the absorption wavelength, may be mentioned. Isopropyl thioxanthone is an example of preferred photosensitizer when an iodonium compound according to the invention is used as photoinitiator.

Amonth the various types of radiations mentioned, ultraviolet radiation is particularly preferred. On the one hand, it is more conveniently used than other mentioned radiations. On the other hand, photoinitiators are in general directly sensitive towards UV rays and photosensitizers are more efficient when the difference of energy ($\delta\lambda$) is lower.

The ionic compounds of the invention may also be used in association with initiators of the radical type which are produced thermally or by actinic radiation. It is thus possible to polymerize or cross-link mixtures of monomers or prepolymers containing functions for which the modes of polymerization are different, for example, monomers or prepolymers which can undergo free radical polymerization and monomers or prepolymers which can undergo cationic polymerization. This possibility is particularly advantageous to produce interpenetrated networks having physical properties which are different from those which would be obtained by mere mixture of polymers produced from corresponding monomers. Vinyl ethers are not or are very lightly active by free radical initiation. It is therefore possible in a reaction mixture containing a phonoinitiator according to the invention, a free radical initiator, at least one monomer of the vinyl ether type and at least one monomer comprising non-activated double bonds such as those of the allyl groups, to carry out a separate polymerization for each type of monomer. On the other hand, it is known that monomers which are electron deficient, such as esters or amides of fumaric acid, maleic acid, acrylic or methacrylic acid, itaconic acid, acrylonitrile, methacrylonitrile, maleimide and derivatives thereof, form in the presence of electron enriched vinyl ethers, charge transfer complexes giving alternate polymers 1:1 by free radical initiation. An initial excess of vinyl monomers with respect to this stoichiometry enables to preserve polymerizable functions by pure cationic initiation. The setting in motion of the activity of a mixture of a free radical initiator and a cationic initiator according to the invention may be carried out simultaneously with the two reactants in the case, for example of a treatment with actinic radiation of a wavelength for which the photoinitiators of the invention and the selected free radical initiators are active, for example at $\lambda=250$ nm. By way of example, initiators that may be mentioned include the following commercial products: Irgacure 184®, Irgacure 651®, Irgagure 261®, Quantacure DMB®, Quantacure ITX®.

It may also be advantageous to use the two modes of polymerization in a sequential manner, to first form prepolymers which are easily produced and whose hardness, adhesiveness, solubility as well as degree of cross-linking may be modified by initiating the activity of the cationic initiator. For example, a mixture of a thermodissociable free radical initiator and a cationic photoinitiator according to the invention enables to obtain sequential polymerizations or cross-linkings, first under heat treatment, then under the action of actinic radiation. In a similar manner, if a free radical initiator and a cationic photoinitiator according to the invention are selected, the first being photosensitive towards wavelengths which are longer than those which activate the photoinitiator according to the invention, there is obtained a cross-linking in two controllable steps. Free radical initiators may, for example, include Irgacure®651 enabling to initiate free radical polymerizations at wavelengths of 365 nm.

It is also an object of the invention to provide for the use of ionic compounds $A^+X^-$ or $(A^+X^-)_p$ of the invention for reactions of chemical amplificlation of photoresists to be used in microlithography. During such use a film of a material comprising a polymer and an ionic compound according to the invention is subject to radiation. The radiation causes the formation of the acid HX which catalyzes the decomposition or conversion of the polymer. After decomposition or conversion of the polymer on parts of the film which have been radiated, the monomers formed or the converted polymer are removed and there remains an image of the unexposed parts. For this particular application it is advantageous to use polymer compounds comprising vinyl units carrying an ionic substituent. Among these compounds, polyiodonium salts having Formula (II), polysulfonium salts having Formula (VI), polyacylsulfonium having Formula (XI), polydiazonium having Formula (XV), salts of organometallic complexes having Formula (VIII), may be mentioned. After photolysis these compounds make it possible to obtain products which are not volatile, and consequently that produce no smell when dealing with sulfides. Among the compounds of the invention, those which are particularly preferred include polysulfoniums which are particularly efficient as photoinitiator, phenacylsulfonium and polymers and copolymers of vinyl ferrocenium which may easily be obtained. Among the polymers which may thus be modified in the presence of a compound of the invention, polymers containing units of ester or arylether of tertiary alcohol, for example poly (phthaldehydes), polymers of bisphenol A and a diacid, poly(tert-butoxycarbonyloxystyrene), poly(tert-butoxy-α-methylstyrene), poly(ditert-butylfumarate-co-allyltrimethylsilane) and polyacrylates of a tertiary alcohol, in particular tert-butyl polyacrylate, may be mentioned. Other polymers are described in J.V. Crivello et al, chemistry of Materials 8, 376–381, (1996).

The ionic compounds $A^+X^-$ or $(A^+X^-)_p$ of the present invention which have an elevated thermal stability, have many advantages as compared to the known salts of the prior art The present invention is described hereinafter more in detail by the following examples given only as illustration.

EXAMPLE 1

To 100 ml of a solution of deionized water containing 15 g of potassium bis-fluorosulfonimide, $KN(SO_2F)_2$ and kept at 0° C. are added 21 g ($1.43 \times 10^{-3}$ moles) of diphenyl-iodonium chloride, $(C_6H_5)_2ICl$. The mixture is stirred for 1 hour away from light. The precipitate which corresponds to diphenyl-iodonium bis-fluorosulfonylimide, $[N(SO_2F)_2]^-$—$[(C_6H_5)_2I]^+$, was separated by filtration, washed in cold water and dried under vacuum. yield: 91% (27.8 g).

Elementary analysis: H: 2.2%; C: 31.4%; N: 3%; F: 8.24%; S: 14.1%; I: 27.6%.

EXAMPLE 2

0.16 g of lithium hydride are suspended in 25 ml of anhydrous THF. 1.53 ml of trifluoroethanol are added dropwise while stirring. At the end of the reaction and hydrogen release, the solution is filtrated and cooled at 0° C. 2.03 g of sodium bis-fluorosulfonylimide, $NaN(SO_2F)_2$, are then added by portions. After 1 hour of reaction at 25° C. a lithium fluoride precipitate is separated by centifugation. The solvent is eliminated by means of a rotary evaporator and the product is dissolved in 50 ml of water, filtrated and 3.2 g of diaryliodonium chloride, $(C_6H_5)_2ICl$, are added. The precipitate is stirred at 0° C. for 2 hours away from light and separated by filtration, followed by washing with cold water and drying under vacuum. 7.2 g (yield 88%) of $[(CF_3CH_2O)_2SO_2N]^-[(C_6H_5)_2I]^+$ are obtained.

EXAMPLE 3

A sample of (4-octyloxyphenyl)phenyl iodonium toluene-sulfonate (in short C8-O-iodonium) was prepared according to the method of Crivello et al (*J. Polym. Sci: Part A: Polymer Chemistry*, (1989), 27, 3951–3968) by reacting hydroxytosyloxyiodobenzene with octyloxybenzene in a mixture of acetonitrile and acetic acid. Octyloxybenzene was previously obtained by reacting sodium phenate with bromooctane in a water/toluene mixture by phase transfer catalysis in the presence of tetrabutyl ammonium bromide. To 8 g of this compound in solution in 60 ml of methylethylketone (MEK) are added 3.02 of potassium bis-fluorosulfonylimide. The mixture is stirred magnetically for 1 hour at room temperature and filtrated to remove the insoluble potassium toluenesulfonate. The solution is poured into a flask which is adjusted to be adapted on a rotary evaporator and the solvent is evaporated. The last traces of MEK are eliminated under a vacuum primary pump and the residue is in the form of a viscous oil (8.04 g, 98%). There is added thereto an equal weight of dichloromethane enabling to give a fluid mixture which can be handled. Solubility tests are made in adjusted flasks after adding a given quantity of mixture and evaporation of the volatile fraction ($CH_2Cl_2$). Results of the tests are given below:

| solvent→ | $CH_2Cl_2$ | MEK | DVE-3 | CDMDVE | E + DVE-3 1:1 |
|---|---|---|---|---|---|
| solubility | □ | □ | s | s > 10% | s > 10% |
| solvent → | toluene | BVE-1 | photo-1 | PDMS 10 | PDMS 500 |
| solubility | s | s | c > 1% | s > 2% | s > 1% |

□ = complete miscibility
s = solubility - 20% by weight
c = compatible (absence of microseparation of optically visible phase)
DVE3 = triethylene glycol divinyl ether
BVE-1 = butanediolmonovinylether
photo-1 = resin for resist with chemical amplification: poly(t-butoxycarboxystyrene- co- cyanoethylacrylate) 1:1
PDMS 10 = a,∞-trimethylsiloxy-polydimethylsiloxane; viscosity 10 cSt, $M_W$ 1250
PDMS 500 = dito; viscosity 500 cSt, $M_W$ 17250

This example shows the excellent properties of solubility of these salts, in particular in solvents, monomers and polymers of low polarity and of hydrophobic character. Similar results are obtained with salts of bis-fluorosulfonimide of (dodecyloxyphenyl)phenyl iodonium (C12-iodonium) and of (octadecyloxy phenyl)phenyl-iodonium (C18-O-iodonium) having aliphatic chains respectively of 12 and 18 carbon atoms.

EXAMPLE 4

19.3 g of 2-ethylhexyl-magnesium prepared from 2-ethylhexyl bromide, are reacted with 15.7 g of bromobenzene in the presence of a catalyst based on bis[bis(diphenylphosphionethane]palladium(0). 19 g of 2-ethylhexyl-benzene thus obtained were dissolved in 60 ml of an equal volume mixture of trifluoroacetic acid and anhydride maintained at 0° C. under stirring, to which 3.5 g of sodium iodide and 4.2 g of iodic anhydride are added. The solvent is removed with a rotary evaporator. Then the residual product is dissolved in 30 ml of acetonitrile and poured in 200 ml of water containing 10 g of sodium acetate and 2 g of sodium sulfite and 14 g of potassium bis-fluorosulfonylimide. The organic phase is extracted with dichloromethane and washed with water. The solvent is eliminated by means of a rotary evaporator to leave an oily liquid of bis-fluorosulfonylimide of bis-[4-(2-ethylhexyl)] phenyl-iodonium. This ionic compound presents characteristics of solubility in hydrocarbons and silicon oils comparable to those of compounds with longer alkyl chains such as bis(dodecylbenzene) iodonium associated to the anion $PF_6^-$. It has a lipophilic character more noticeable than that of the compound of Example 3. It is particularly advantageous to catalyze the cross-linking of antiadhesive silicon coating and the polymerization of the monomers of low polarity such as cyclohexanedimethanoldivinylether, 2-ethylhexylglycidylether or 2-ethylhexylvinylether.

EXAMPLE 5

To 40 g of allyloxybenzene in 50 ml of acetic acid are added dropwise 78.4 g of phenyliodosotoluene sulfonate in 100 ml of acetic acid and the mixture is stirred at room temperature for 2 hours. The reaction mixture is poured into 1l of dioxane, the precipitate of (allyloxyphenyl)-phenyliodonium toluenesulfonate obtained is washed with ether and dried. Conversion into bis-fluorosulfonylimide is carried out by mixing 15 g of (allyloxyphenyl)-phenyliodonium toluenesulfonate and 7 g of KN(SO$_2$F)$_2$ in 150 ml of water at 0° C. The salt is extracted with 2×50 ml of dichloromethane and the solvent is evaporated. The residual salt (consisting of (allyloxyphenyl)-phenyliodonium bis-fluorosulfonylimide) is diluted with 60 ml of THF and is introduced into a three-neck flask provided with a cooler, a mechanical stirrer and a neutral gas inlet (Argon), said flask containing 8.5 g of a copolymer of dimethylsiloxane and (hydrogeno)(methyl)-siloxane (HMS 301 25% SiH, M$_w$ 1900 sold by Gelest Inc., Tullytown, Pa., U.S.A.) in solution in 60 ml of THF and 90 mg of chloroplatinic acid H$_2$PtCl$_6$. The mixture was heated under reflux for 2 hours. 1 g of 1-hexene was thereafter added and the reaction was continued for 1 hour. A sampling enables to confirm the complete disappearance of IR bands of the SiH bond which confirms hydrosilylation between the allyl groups of (allyloxyphenyl)-phenyliodonium bis-fluorosulfonylimide and groups SiH of the copolymer of dimethylsiloxane and (hydrogeno)(methyl)-siloxane. The polymer thus obtained which contains ionic pendant groups is precipitated in methanol and purified by means of three operations of dissolution (THF)/precipitation (methanol and ether).

EXAMPLE 6

6.5 g of trifluoromethanesulfonamide CF$_3$SO$_2$NH$_2$ and 10.8 ml of pyridine in 60 ml of dichloromethane are cooled at −15° C. and 3.6 ml of sulfuryl chloride in 10 ml of dichloromethane, and 4.6 ml of 1,1,1,3,3,3-hexafluoro-2-propanol are added dropwise. The mixture is stirred for 1 hour at −15° C., then for 4 hours at room temperature (25° C.). The reaction mixture is filtered and the solvent is removed with a rotary evaporator; the solid residue obtained was dissolved in 50 ml of water containing 5 g of sodium acetate; 18.45 g of finely pulverized bis[4-(diphenylsulfonio)-phenyl]thioether bis (hexafluorophosphate) (previously prepared according the method of Akhtar et al. (Chem. Mat. (1990), 2, 732 and K. T. Chang, U.S. Pat. No. 4,197,174) were added, and the mixture was stirred at room temperature for 3 hours in a roller crusher in a flask of rigid polyethylene containing zirconium oxide balls. The suspension obtained was filtrated and the resulting solid was dried. There is thus obtained 28 g (yield: 78%) of a compound of the following formula.

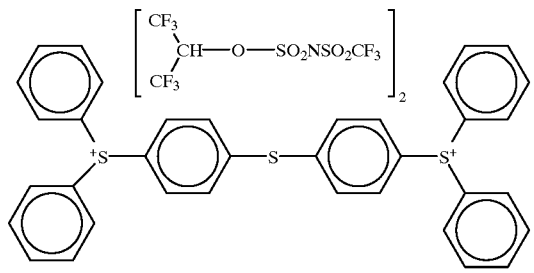

EXAMPLE 7

Bis(4-fluorophenyl)-[4(4-benzoylphenylthio)phenyl] sulfonium methanesulfonate was prepared according to the method of Abe et al (U.S. Pat. No. 5,534,557) by a Friedel-Craft reaction between benzoic acid and diphenyl-thioether, and by condensation in Eaton reactant (P$_2$O$_5$/CH$_3$SO$_3$H) (J. Org. Chem. (1973), 38, 4071) in the following manner: 15 g of 4-benzoyl-diphenylthioether, 12.4 g of 4,4'-difluorodiphenylsulfoxide, 20.6 g of phosphorus pentoxide were dissolved in 206 g of methane sulfonic acid and the reaction mixture was kept at 80° C. for 3 hours.

The solution containing bis-(4-fluorophenyl)-[4(4-benzoylphenylthio)phenyl]sulfonium methanesulfonate which was formed during the rection was poured into 700 ml of water containing 200 g of sodium acid and 12 g of potassium bis-fluorosulfonylimide. The precipitate of bis(4-fluorophenyl)-[4-(4-benzoylphenylthio)phenyl)sulfonium which was produced was separated by filtration and recrystallized in 2-propanol. Elementary analyses: H: 3.06%; C: 53.8%; N: 2.03%; F: 11%; S: 18.6%.

EXAMPLE 8

13.2 g of sodium thiophenate and 19.04 g of 9,10-dibromoanthracene were dissolved in 100ml of N-methylpyrrolidone at 180° C. The reaction product (DPA) was washed with water and recrystallied in a chloroform/ethanol mixture.

6 g of DPA, 4.2 g of bromobutane and 10 g of potassium tris(fluorosulfonyl)methylide were heated in 40 ml of MEK in a sealed flask at 60° C. for 24 hours, and the resulting mixture was filtrated to remove the insoluble potassium bromide. The solvent was removed by means of a rotary evaporator. There was obtained a salt having the structural formula:

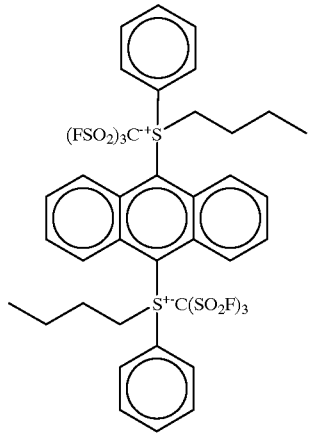

This salt is much more active, in required mass fraction, as well as in polymerization kinetics, than the conventional sulfonium salts. Contrary to the method of preparation described in Hacker et al (U.S. Pat. No. 4,760,013) for the salt SbF$_6^-$, no silver salt is required for the preparation of this compound because of the solubility of the salts derived from the anions of the present invention in solvents where alkali halides are completely insoluble.

EXAMPLE 9

A polyether was prepared by reacting 15 g of dimercaptohexane with 18.67 g of 1,2-bis(2-chloroethoxy)ethane in 200 ml of N-methylpyrrolidone at 150° C. in the presence of 10 g of potassium carbonate. The polymer is precipitated in water and purified by means of a plurality of operations of dissolution (THF)/precipitation (diethylether) and separation by centrifugation in a single container. The polymer is in the form of sticky mass.

In a three-neck flask provided with a cooler, a mechanical stirrer and a neutral gas inlet (Argon), 7 g of the polymer are dissolved in 120 ml of dichloromethane ($CH_2Cl_2$) and 4.8 g of 2-bromoacetophenone are added dropwise. The mixture was heated under reflux at 40° C. A precipitate rapidly appeared. The reaction was continued 12 hours after the appearance of the precipitate. The polyphenacylsulfonium bromide was separated by filtration and washed with dichloromethane and ether.

5 g of the polyphenacylsulfonium bromide were dissolved in 60 ml of water, the solution was filtrated and 2.5 g of potassium bis(fluorosulfonyl)imide $K(FSO_2)_2N$ in 25 ml of water were added under stirring. A precipitate was immediately formed and stirring was continued for 1 hour. The polyphenacylsulfonium bisfluorosulfonylimide polymer was separated by filtration and dried (quantitative yield).

| solvent | Acetone | $C_2H_4Cl_2$ | MEK | DVE-3 | epoxy /DVE3 |
|---|---|---|---|---|---|
| solubility | soluble | s | s | s > 3% | s > 3% |

DVE-3 = triethylene glycol divinyl ether
MEK = methylethylketone

EXAMPLE 10

The properties of solubility of certain polyionic compounds of the present invention have been compared to the properties of a poly(iodonium) prepared according to Crivello & Lam (*J. Polym. Sci.; Polymer Chemistry*, (1979), 17, 3845–3858). The polyiodonium according to Crivello et al was obtained by trans-addition of (4,4'-N-maleimido) diphenyliodonium chloride to 1,10 decanethiol in m-cresol in the presence of a tertiary base, followed by metathesis in the presence of $NaPF_6$. The compounds of the present invention have been prepared in the same manner, but by replacing for the metathesis, $NaPF_6$ by one of the following salts: $Na^+(FSO_2)_2N^-$, $Na^+[(CF_3)_2CHOSO_2]_2N^-$, $Na^+(FSO_2)_3C^-$. The results are given in the following Table.

| anion solvent → | Acetone | $C_2H_4Cl_2$ | MEK | NMP | PEPC |
|---|---|---|---|---|---|
| $(FSO_2)_2N^-$ | soluble | s | s | S | s |
| $[(CF_3)_2CHOSO_2]_2N^-$ | s | s | s | s | s |
| $(FSO_2)_3C^-$ | s | s | s | s | s |
| $PF_6$ | insoluble | i | i | i | i |

MEK = methylethylketone
PEPC = propylene carbonate + ethylene carbonate
NMP = N-methylpyrrolidone Noted differences of solubility were also observed with linear polysulfonium salts described by Kuczinski (U.S. Pat. No. 5,550,171) which are only soluble in solvents in which the solubility parameter is equal to 22 $MPa^{1/2}$, corresponding to N-methylpyrrolidone NMP and to propylene carbonate. The photoinitiators obtained by replacing the anion $MF_6^-$(M=P, As, Sb) with those of the invention such as $(FSO_2)_2N^-$ or $[(CF_3)_2CHOSO_2]_2N^-$ become soluble in common and easy-to-use solvents having solubility parameters lower than 15 $MPa^{1/2}$ such as methylethylketone, acetone, acetonitrile.

EXAMPLE 11

10 g of (cumene)cyclopentadienyl-iron hexafluorophosphate (Irgacure 261, Ciba-Geiby, Switzerland) (noted $[[Fe]]^+PF_6^-$) have been dissolved in 50 ml of dichloroethane. To this solution 5.7 g of potassium bis-fluorosulfonylimide in solution in 15 ml of nitromethane were added. The mixture was stirred 1 hour and potassium hexafluorophosphate $KPF_6$ was separated by filtration. The solvent was removed by means of a rotary evaporator to leave an orange powder consisting of (cumene) cyclopentadienyl-iron, bis-fluorosulfonylimide, very soluble in common solvents and vinyl monomers.

The results of solubility tests are given hereinafter.

| solvent → | Acetone | MEK | DVE-3 | CDMDVE | E + DVE-3 1:1 |
|---|---|---|---|---|---|
| $[[Fe]]^+(FSO_2)_2N^-$ | soluble | s | s | s > 8% | s > 5% |

CDMDVE = cyclohexanedimethanoldivinylether
E = bisphenol A diglycidylether
DVE-3 = triethylene glycol divinyl ether
MEK = methylethylketone Using the same process, 10 g of Irgacure 261 and 7 g of potassium (fluorosulfonyl)(trifluoromethanesulfonyl)imide $K(FSO_2)NSO_2CF_3$ are reacted to give cumene (cyclopentadienyl-iron (fluorosulfonyl) (trifluoromethanesulfonyl)imide $[[Fe]]^+[(FSO_2)NSO_2CF_3]^-$ in a quantitative manner.

EXAMPLE 12

1 ml of bromine diluted in 5 ml of acetonitrile was added to 10 g of butylferrocene (Aldrich, Milwaukee U.S.A.) in solution in 50 ml of acetonitrile maintained at 0° C. To the blue solution obtained, 9.5 g of potassium bis-fluorosulfonylimide have been added. The mixture was stirred 1 hour and the precipitate of potassium bromide was separated by filtration. The solvent was removed by means of a rotary evaporator. There is obtained a dark blue oil which recrystallizes by grinding with ether. The butylferricinium bis-fluorosulfonylimide obtained in the form of crystals was washed with ether and kept away from light.

Elementary analysis: H: 4.7; C: 43.8; N: 3.65; F: 14.8; S: 16.8.

EXAMPLE 13

3.4 g of [bis(trifluoroacetoxy)iodo]benzene were added to 5 g of 1,2-diferrocenylethane (sold by Aldrich Co., Milwaukee, U.S.A.) in solution in 50 ml of toluene. A blue precipitate is immediately formed. It was separated, washed with ether and dried. 5 g of the solid obtained were placed in solution into 25 ml of water and 3.6 g of potassium bis(fluorosulfonyl)imide were added. The precipitate of ferrocene dimer in the form of a salt of the imide anion was obtained with a quantitative yield in the form of a blue crystalline product.

EXAMPLE 14

To 6 g of a copolymer of vinylferrocene (sold by Aldrich Co., Milwaukee, U.S.A.) and butyl methacrylate containing 42% organometallic units obtained by free radical polymerization induced by azobis(butyronitrile) in solution in toluene, there were added 3.3 g of [bis(trifluoroacetoxy) iodo]benzene (sold by Aldrich). A blue precipitate is immediately formed and it was separated, washed with ether to remove the excess of oxidizing agent and dried. 5 g of this poly(ionic) compound of ferricinium associated to the trifluoroacetate anion were placed in suspension in 25 ml of water to which there were added 2.2 g of potassium bis (fluorosulfonyl)imide. The precipitate of poly(ionic) compound of the imide anion of polyferricinium was obtained in a quantitative yield in the form of a blue amorphous powder which is soluble in most of the common solvents.

EXAMPLE 15

An oligomer of diazonium was prepared according to the method described in U.S. Pat. No. 2,714,066 by condensation of 4-diazodiphenylamine chlorozincate with formaldehyde. 25 g of this poly(ionic) compound were dissolved in 500 ml of water maintained at 0° C. and containing 50 g of sodium acetate and 28 g of a di-sodium salt of ethylenediaminetetraacetic acide (EDTA). 17 g of potassium salt of bis(fluorosulfonyl)imide in solution in 50 ml of water were then added. The poly(ionic) compound was separated by filtration and dried (quantitative yield), and maintained at 0° C. away from light. This compound is very soluble in the common organic solvents of average polarity such as MEK, and is soluble in monomers of type DVE-3 or PEPEC and glycidyl ethers.

EXAMPLE 16

Negative Photoresist 2 g of poly(4-hydroxystyrene)-c-styrene (8:2) (sold by Shinetu, Japan) in solution in 20 ml of dimethylformamide were added to 9.7 ml of a 1 M solution of potassium hydroxide in methanol containing 1.3 g of chloroethylvinylether. The solution was heated at 80° C. for 1 hour and the reaction mixture was poured into 100 ml of water where the poly(4-vinyloxyethyl)-styrene-co-styrene formed has precipitated. The polymer was purified in a plurality of operations of dissolution precipitation in acetone (solvent)/water (precipitant) and acetone (solvent/ether (precipitant).

1 g of poly(4-vinyloxyethyl)-styrene-co-styrene and 20 mg of polymer of Example 5 in 10 ml of MEK were spin-coated on a silicon substrate so as to form a film 0.5 μm thick. The film was subjected to an exposure of 1 MJ/cm$^2$ obtained by a laser KrF through an interferential mask. The development was carried out with THF. The resolution obtained, observed with an electronic microscope (SEM) is of the order of the thickness of the film, i.e., 0.5 μm. This photoresist contains no metallic element capable of contaminating silicon.

EXAMPLE 17

Positive Photoresist 1 g of poly(4-t-butoxycarboxystyrene) in dichloroethane and 60 mg of polymer of Example 9 were spin-coated on a silicon substrate so as to form a film 0.5 μm thick. The film was subjected to an exposure of 1 MJ/cm$^2$ obtained with a laser KrF through an interferential mask. The development was carried out with a solution of 4% tetramethyl ammonium hydroxide in water. The resolution obtained, observed with an electronic microscope (SEM) is of the order of the thickness of the film, i.e., 0.5 μm. This photoresist contains no metallic element capable of contaminating silicon.

EXAMPLE 18

The properties of photo-initiation of the products of the invention are illustrated by the results gathered in the following Table. The polyionic compounds of the preceding Examples were used at the rate of 1% by weight in different monomers and were radiated with UV radiation at 254 nm with a power of 1900 mW/cm$^2$ for 5 seconds, followed by a period of 10 minutes enabling the species produced to propagate in the medium (postcure).

| monomer photo-initiator | DVE3 | Epoxy + DVE3 | CHDM + 10% PEPC | cyclohexene-epoxide polysiloxane* | α-methyl-styrene |
|---|---|---|---|---|---|
| Ex. 1  | ++ | ++ | ++ |   |   |
| Ex. 2  | ++ | ++ | ++ | + |   |
| Ex. 3  | ++ | ++ | +  | + | + |
| Ex. 4  | ++ | ++ | +  | + | + |
| Ex. 5  | ++ | ++ | +  | + | + |
| Ex. 6  | ++ | ++ | +  | + |   |
| Ex. 7  | ++ | ++ | +  | + |   |
| Ex. 8  | ++ | ++ | +  | + |   |
| Ex. 9  | ++ | ++ | +  | + | + |
| Ex. 10 | ++ | ++ | +  |   |   |
| Ex. 11 | ++ | ++ | +  | + | + |
| Ex. 12 | ++ | ++ | +  | + |   |
| Ex. 13 | ++ | ++ | +  | + |   |
| Ex. 14 | ++ | ++ | +  | + |   |
| Ex. 15 | ++ | ++ | +  | + |   |

*cross-linking
++highly exothermic polymerization giving a colored polymer
+polymerization giving a non-sticking resin

We claim:

1. An ionic compound comprising at least one group A$^+$X$^-$, comprising:
    a cationic group A$^+$ selected from the group consisting of biaryliodonium, arylsulfonium, arylacylsulfonium, diazonium and organometallic cations comprising a transition metal complexed with at least one unsaturated cyclic group comprising 4–12 carbon atoms, said cationic group A$^+$ being part of a polymer chain;
    X$^-$ is an imide anion selected from the group consisting of [FSO$_2$NSO$_2$R'$_F$]$^-$, [R$_F$CH$_2$OSO$_2$NSO$_2$R'$_F$]$^-$ and [(R$_F$)$_2$CHOSO$_2$NSO$_2$R'$_F$]$^-$, or a methylide anion selected from the group consisting of [FSO$_2$C(Q)SO$_2$R'$_F$]$^-$, [R$_F$CH$_2$OSO$_2$C(Q)SO$_2$R'$_F$]$^-$ and [(R$_F$)$_2$CHOSO$_2$C(Q)SO$_2$R'$_F$]$^-$ in which:
    1) Q represents:
        H$^-$, Cl$^-$, F$^-$, Br$^-$ or CN$^-$;
        an alkyl radical having 1–30 carbon atoms;
        an aryl, alkylaryl or arylalkyl radical having 6–30 carbon atoms;
        a group R"$_F^-$, a group R"$_F$SO$_2^-$, a group R"$_F$CH$_2$O—SO$_2^-$ or a group (R"$_F$)$_2$CHO—SO$_2^-$;
    2) R$_F$, R'$_F$ and R"$_F$ are such that when X$^-$ is a methylide anion, these groups are independently selected from the group consisting of fluorine, perhaloalkyl groups having 1–30 carbon atoms, (perhaloalkyl)alkoxy groups having 2–30 carbon atoms, perhalogenated cycloaliphatic groups having 3–30 carbon atoms containing heteroatoms selected from the group consisting of O and N and/or containing at least one perhaloalkyl chain, and perhalogenated aryl groups having 6–30 carbon atoms; or
    3) R$_F$ and R'$_F$ together form a bivalent radical selected from the group consisting of perfluorinated linear alkylene radicals having 2–8 carbon atoms; or
    4) when X$^-$ is a methylide anion, R'$_F$ and R"$_F$ together form a bivalent methylide anion radical selected from the group consisting of perfluorinated linear alkylene radicals having 2–8 carbon atoms, or R$_F$ and R"$_F$ together form a bivalent methylide anion radical selected from the group consisting of perfluorinated linear alkylene radicals having 2–8 carbon atoms.

2. The ionic compound according to claim 1, wherein the anion is a sulfonimide anion having one of the forming formula [FSO$_2$NSO$_2$R'$_F$]$^-$, [CF$_3$CH$_2$OSO$_2$NSO$_2$R'$_F$]$^-$ and

[(CF$_3$)$_2$CHOSO$_2$NSO$_2$R'$_F$]$^-$, or a sulfonylmethylide anion having one of the formula [FSO$_2$C(Q)SO$_2$R'$_F$]$^-$, [CF$_3$CH$_2$OSO$_2$C(Q)SO$_2$R$_F$]$^-$ or [(CFR$_3$)$_2$CHOSO$_2$—C(Q)SO$_2$R'$_F$]$^-$, in which R'$_F$ is F, CF$_3$CH$_2$O$^-$, (CF$_3$)$_2$CH—O$^-$ or a perfluoroalkyl group having 1–10 carbon atoms and Q is selected from the group consisting of hydrogen, FSO$_2^-$, CF$_3$CH$_2$O—SO$_2^-$, (CF$_3$)$_2$CH—O—SO$_2^-$, alkyl, aryl, alkylaryl or arylalkyl groups having at most 30 carbon atoms, perfluoroalkylsulfonyl groups having 1–8 carbon atoms or perfluoroalkyl groups having 1–12 carbon atoms; or Q and R'$_F$ together form a bivalent perfluorinated linear alkylene group having 1–8 carbon atoms.

3. The ionic compound according to claim 1, wherein the anion is selected from the group consisting of (FSO$_2$)$_2$N$^-$, (FSO$_2$)$_3$C$^-$, (FSO$_2$)$_2$CH$^-$, (CF$_3$CH$_2$OSO$_2$)$_2$N$^-$, [(CF$_3$)$_2$CHOSO$_2$]$_2$N$^-$, (CF$_3$CH$_2$OSO$_2$)$_2$CH$^-$, [(CF$_3$)$_2$CHOSO$_2$]$_2$CH$^-$, [(CF$_3$)$_2$CHOSO$_2$]$_3$C$^-$, [(CF$_3$)$_2$CHOSO$_2$]$_3$C$^-$, [FSO$_2$NSO$_2$—CF$_3$]$^-$, [FSO$_2$NSO$_2$C$_2$F$_5$]$^-$, [(CF$_3$)$_2$CHOSO$_2$NSO$_2$CF$_3$]$^-$, [(CF$_3$)$_2$CHOSO$_2$NSO$_2$CF$_3$]$^-$, [(CF$_3$)$_2$CHOSO$_2$NSO$_2$C$_2$F$_5$]$^-$ and [CF$_3$CH$_2$OSO$_2$NSO$_2$C$_2$F$_5$]$^-$.

4. The ionic compound according to claim 1, wherein the cation A$^+$ has the formula

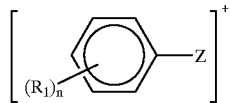

in which Z is selected from the group consisting of:
aryliodonium groups

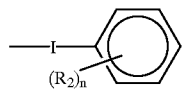

sulfonium groups

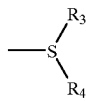

acylsulfonium groups

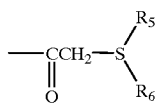

diazonium groups

organometallic groups

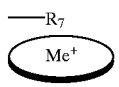

and in which n is an integer of 1–4 and groups R$_1$ to R$_8$ are independently selected from the group consisting of:
linear or branched alkyl or arylalkyl radicals having 1–30 carbon atoms;

alkenyl radicals having 1–30 carbon atoms;

aryl or alkylaryl radicals having 6–30 carbon atoms, including those which have condensed nuclei;

radicals having 1–30 carbon atoms and selected from the group consisting of oxaalkyls, azaalkyls, thiaalkyls, phosphaalkyls, oxaalkylenes, azaalkylenes, thiaalkylenes and phosphaalkylenes, radicals having 1–30 carbon atoms and containing a sulfoxide, sulfone, phosphide oxide or phosphonate group;

aromatic or alicyclic heterocyclic radicals comprising at least one heteroatom selected from the group consisting of O, N, S and P;

—NO, —CN, —OH, —Cl, —Br, —I, —F; and two substituents selected from the group consisting of R$_1$, or two substituents selected from the group consisting of R$_2$, or two substituents selected from the group consisting of R$_3$ and R$_4$, or two substituents selected from the group consisting of R$_5$ and R$_6$ together form a bivalent radical which form a cyclic group, said bivalent radical selected from the group consisting of linear alkylene radicals having 1–18 carbon atoms, benzo biradicals having at least one substituent selected from the group consisting of alkyl, oxaalkyl or alkenyl radicals having 1–10 carbon atoms, oxaalkylene, groups having the formula —R'—(OCH$_2$CH$_2$)$_q$—OR— or —R'—[OCH(CH$_3$)CH$_2$]$_q$—OR'— in which R' is H or a linear alkylene radical having 1–18 carbon atoms and $1 \leq q \leq 22$; and Me$^+$ is a transition metal selected from the group consisting of transition metals of columns 3 to 12 and rows 3 to 6 of the Periodic Table.

5. The ionic compound according to claim 4, wherein the substituents R$_1$ to R$_8$ are independently selected from the group consisting of 2-ethylhexyl, a linear alkyl radical having 1–18 carbon atoms, phenyl, oxaalkyls having formula R—(OCH$_2$CH$_2$)$_y$— or R—[OCH(CH$_3$CH$_2$]$_y$— in which R is H or a linear alkyl radical having 1–18 carbon atoms and $1 \leq y \leq 22$.

6. The ionic compound according to claim 1, which comprises a polycationic part (A$^+$)p comprising a plurality of onium units and a plurality of anions X$^-$ in sufficient number to ensure electrical neutrality to the compound, the onium units being selected from the group consisting of biaryliodonium, arylsulfonium, arylacylsulfonium, diazonium, organometallic cations comprising a transition metal which is complexed with at least one unsaturated cyclic group comprising 4–12 carbon atoms.

7. An ionic polymer consisting of a polyiodonium salt having one of formula (I)–(IV), or a polysulfonium salt having one of formula (V)–(IX), or a polyacylsulfonium salt having one of formula (X)–(XIV), or a polydiazonium salt having one of formula (XV), or an organometallic polyonium salt having one of formula (XVI)–(XX):

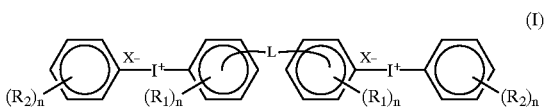

(I)

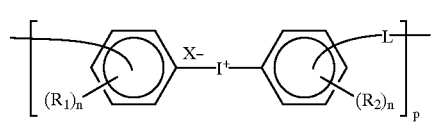
(II)
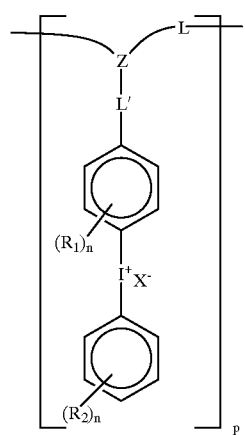
(III)
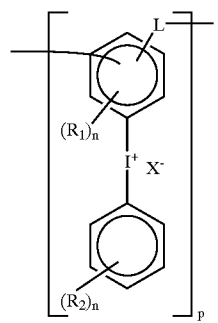
(IV)
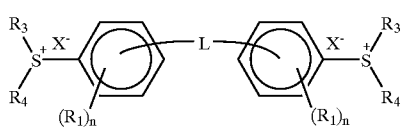
(V)
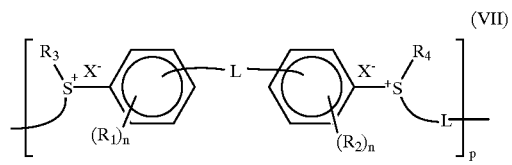
(VII)
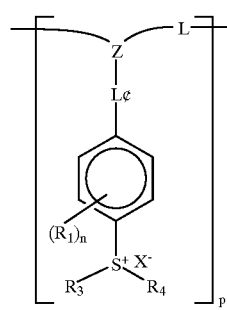
(VI)
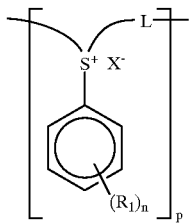
(VIII)
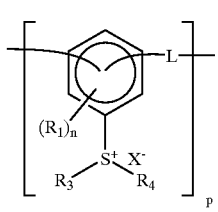
(IX)
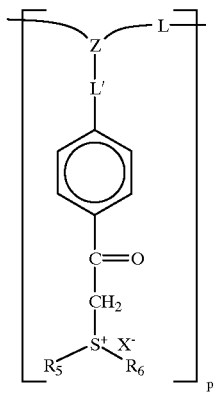
(XI)
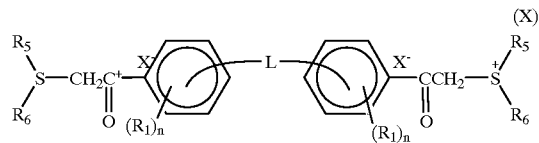
(X)
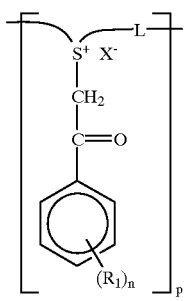
(XIII)

-continued

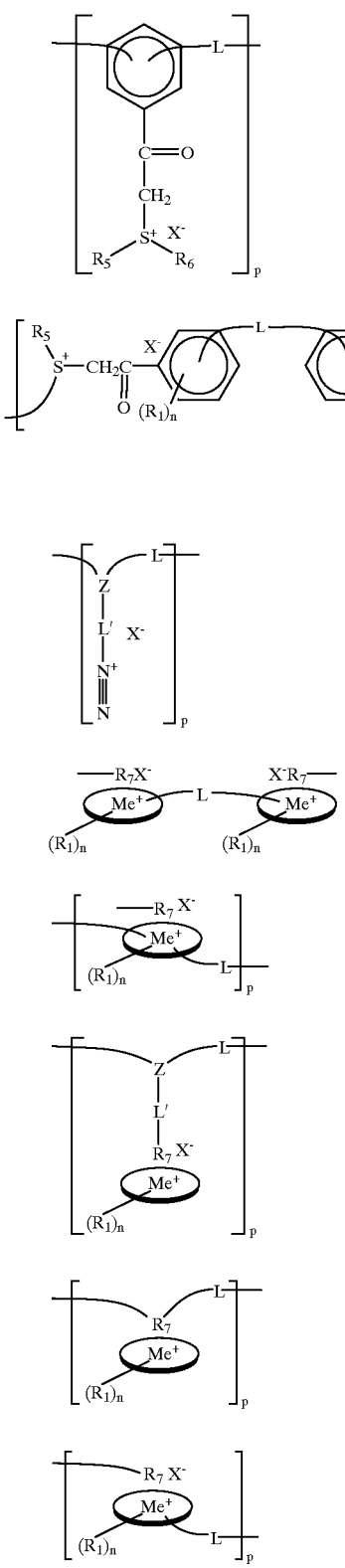

in which:

a1) n is an integer of 1–4 and groups $R_1$ to $R_8$ are independently selected from the group consisting of:

linear or branched alkyl or arylalkyl radicals having 1–30 carbon atoms;

alkenyl radicals having 1–30 carbon atoms;

aryl or alkylaryl radicals having 6–30 carbon atoms, including those which have condensed nuclei;

radicals having 1–30 carbon atoms and selected from the group consisting of oxaalkyls, azaalkyls, thiaalkyls, phosphaalkyls, oxaalkylenes, azaalkylenes, thiaalkylenes and phosphaalkylenes;

radicals having 1–30 carbon atoms and containing a sulfoxide, sulfone, phosphine oxide or phosphonate group, all these radicals being obtained by addition of oxygen on sulfur or phosphorus;

aromatic or alicyclic heterocyclic radicals comprising at least one heteroatom selected from the group consisting of O, N, S and P;

—NO, —CN, —OH, —Cl, —Br, —I, —F; and two substituents selected from the group consisting of $R_1$ and $R_2$, two substituents selected from the group consisting of $R_3$ and $R_4$ or two substituents selected from the group consisting of $R_5$ and $R_6$ together form a bivalent radical which form a cyclic, said bivalent radical being selected from the group consisting of linear alkylene radicals having 1–18 carbon atoms, benzo biradicals carrying at least one substituent selected from the group consisting of alkyl, oxaalkyl or alkenyl radicals having 1–10 carbon atoms, oxaalkylene groups having the formula —R'($OCH_2CH_2$)$_q$—O—R'— or —R'—[$OCH(CH_3)CH_2$]$_q$—O—R'— in which R' is a linear alkylene radical having 0–18 carbon atoms and $1 \leq q \leq 22$;

a2) L' represents a bivalent radical selected from the group consisting of linear alkylene radicals having 1–18 carbon atoms, substituted or non-substituted phenylene groups, oxaalkylene groups having the formula —R'—($OCH_2CH_2$)$_q$—O—R'— or —R'—$OCH(CH_3)CH_2$]$_q$—O—R'— in which R' is a linear alkylene radical having 0–18 carbon atoms and $1 \leq q \leq 22$, —O—, —S—, >C=O, siloxane groups —R'—O—[Si(R)$_2$O ]$_r$—R'— or —O—[Si(R)$_2$O]$_r$— in which $1 \leq r \leq 40$ and in which R' has the meaning given above and R is selected from the group consisting of 2-ethylhexyl, phenyl, linear alkyl radicals having 1–18 carbon atoms, and a direct bond between two carbon atoms of two non-condensed aryl groups;

a3) L represents a bivalent radical selected from the group defined in a2) above for L'; or represents a segment comprising at least one non-ionic monomer unit or having an ionic group which is not sensitive towards the action of actinic radiation, wherein L here represents the average space between the active ionic groups;

a4) p represents the number of recurring units and $2 \leq p \leq 1000$;

a5) Z represents CH, CR, N, SiR, $SiRO_3$, R being selected from the group consisting of 2-ethylhexyl, linear alkyl radicals having 1–18 carbon atoms and phenyl; and a6) $Me^+$ is a complexed transition metal selected from the group consisting of transition elements of columns 3–12 and rows 3–6 of the Periodic Table.

8. A process for the preparation of an ionic polymer compound according to claim 6, consisting of:

conducting a metathesis reaction in water or a water/light alcohol mixture of a salt $(A^+X_1^-)_p$ of polycation $(A^+)_p$ and a compound $A_1^+X^-$, both of which are soluble in the reaction mixture, anion $X_1^{31}$ having a hydrophilic character, and $A_1^+$ being selected from the group consisting of alkali and alkali earth metals wherein $X^-$ is as defined in claim 5.

9. The process according to claim 8, wherein the anion $X_1^-$ is a hydroxide, a chloride, a bromide, a hydrogenosulfate, a dihydrogenophosphate or a methylsulfonate.

10. A process for the polymerization or cross-linking of monomers or prepolymers capable of cationic reaction, comprising:

conducting said polymerization or cross-linking in the presence of a photoinitiator constituting a source of acid catalyzing the reaction, said photoinitiator being a compound of claim 1.

11. The process according to claim 10, wherein the monomers are selected from the group consisting of compounds containing a cyclic ether moiety, a cyclic thioether moiety, a cyclic amine moiety, 1,1-dialkylethylenes, aromatic vinyl monomers, N-vinyl compounds, vinyl ethers, oxazolines, lactones and lactams.

12. The process according to claim 10, wherein the prepolymer is selected from the group consisting of prepolymers formed from epoxy group bearing aliphatic, aromatic, or heterocyclic monomers.

13. The process according to claim 10, which consists in mixing the photoinitiator with at least one monomer or prepolymer capable of cationic polymerization, and subjecting the mixture obtained to actinic or β-radiation.

14. The process according to claim 13, wherein the reaction mixture is subject to radiation after having been formed into a thin layer.

15. The process according to claim 10, wherein the quantity of photoinitiator ranges from 0.01–15% by weight with respect to weight of the monomer or prepolymer.

16. The process according to claim 10, wherein the photoinitiator is present as a solution in a solvent which is inert toward the polymerization reaction.

17. The process according to claim 16, the solvent is selected from the group consisting of acetone, methyl-ethyl ketone, acetonitrile, propylene carbonate, γ-butyrolactone, ether-esters of mono-, di-, triethylene or propylene glycols, ether-alcohols of mono-, di-, triethylene or propylene glycols and esters of phthalic acid or citric acid.

18. The process according to claim 10, wherein the reaction is conducted in the presence of a solvent or a diluent consisting of a compound which is reactive toward the polymerization reaction.

19. The process according to claim 18, wherein the compound is selected from the group consisting of vinyl mono- and di-ethers of mono-, di-, tri-, tetra-, ethylene or propylene glycols, the trivinyl ether of trimethylopropane, the divinylether of dimethanol-cyclohexane, N-methylpyrrolidone and the 2-propenylether of propylene carbonate.

20. The process according to claim 10, wherein a photosensitizer is added to the reaction mixture.

21. The process according to claim 20, wherein the photosensitizer is selected from the group consisting of anthracene, diphenyl-9,10-anthracene, perylene, phenothiazine, tetracene, xanthone, thioxanthone, isopropylthioxantone, acetophenone, benzophenone, 1,3,5-triaryl-2-pyrazolines and derivatives thereof substituted on the aromatic nuclei by alkyl, oxa- or azaalkyl radicals.

22. The process according to claim 10, wherein the reaction mixture additionally contains at least one monomer or prepolymer capable of free radical polymerization and a compound capable of releasing an initiator of free radical polymerization under actinic or β-radiation or under heat.

23. A process for modifying the solubility properties of a polymer having groups which are reactive towards acids, consists of:

subjecting said polymer to actinic radiation or β-radiation, in the presence of the compound of claim 1.

24. The process according to claim 23, wherein the polymer contains ester or arylether of tertiary alcohol units.

25. The process according to claim 24, wherein the polymer is selected from the group consisting of tert-butyl polyacrylates, tert-butyl polyitaconates, poly(tert-butoxycarbonyloxystyrene) and poly(tert-butoxystyrene).

26. The process according to claim 23, wherein said compound is a compound having one of formula (III), (VI), (IX), (XV) or (XVIII), as set forth in claim 6.

* * * * *